United States Patent [19]

Chamberlain et al.

[11] Patent Number: 5,194,263
[45] Date of Patent: Mar. 16, 1993

[54] PARTICULATE MATERIALS, THEIR PRODUCTION AND USE

[75] Inventors: Peter Chamberlain; John G. Langley, both of West Yorkshire, England

[73] Assignee: Allied Colloids Limited, England

[21] Appl. No.: 749,695

[22] Filed: Aug. 26, 1991

Related U.S. Application Data

[63] Continuation-in-part of Ser. No. 467,668, Jan. 19, 1990, abandoned.

[30] Foreign Application Priority Data

Jan. 20, 1989 [GB] United Kingdom ................. 8901254

[51] Int. Cl.$^5$ ............................................. A01N 25/00
[52] U.S. Cl. ...................................... 504/347; 514/89; 504/116; 71/DIG. 1; 424/405
[58] Field of Search ............... 71/90, 92, 103; 514/89; 424/405

[56] References Cited

U.S. PATENT DOCUMENTS

| | | | |
|---|---|---|---|
| 4,233,057 | 11/1980 | Lavanish | 71/90 |
| 4,303,642 | 12/1981 | Kangas | 514/89 |
| 4,589,914 | 5/1986 | Cartwright | 71/103 |
| 4,758,670 | 7/1988 | Muller | 71/92 |
| 5,043,163 | 8/1991 | Pap | 424/405 |

FOREIGN PATENT DOCUMENTS

| | | |
|---|---|---|
| 0379379 | 1/1990 | European Pat. Off. . |
| 1475229 | 6/1977 | United Kingdom . |
| 1507739 | 4/1978 | United Kingdom . |

Primary Examiner—Thurman K. Page
Assistant Examiner—William E. Benston
Attorney, Agent, or Firm—Ostrolenk, Faber, Gerb & Soffen

[57] ABSTRACT

Agrochemical and other particulate compositions are formed by coacervation. The coacervate is preferably formed from two water soluble coacervating polymers and stabilizes the particles against agglomeration. The coacervate is preferably formed from a relatively low molecular weight cationic polymer and a relatively high molecular weight anionic polymer.

41 Claims, No Drawings

PARTICULATE MATERIALS, THEIR PRODUCTION AND USE

This invention is a continuation-in-part of U.S. application Ser. No. 467,668 filed Jan. 19, 1990 by Peter Chamberlain and John Graham Langley and now abandoned.

The parent application, the corresponding European publication EP-A-379379 and the present application all relate primarily to agricultural particulate compositons that may be powders but are preferably aqueous dispersions. However in their broader aspect, they all relate to particulate compositions, for instance dispersions, which are convenient and safe to handle and by which active ingredients can be delivered to a chosen place of use. The active ingredients may be, for instance, materials such as pesticides or other agriculturally useful compounds (agrochemicals), pharmaceuticals or perfumes. The invention is of particular value when applied to the formulation of water insoluble pesticides and other water-insoluble, agrochemicals.

It is frequently necessary to formulate the compound as a concentrate that can be diluted at the point of use to form a sprayable composition. When the compound is water soluble, the concentrate can be a concentrated aqueous solution or a water soluble granule or other soluble solid. However many agriculturally useful compounds are insoluble in water. It is generally preferred that they should be applied by spraying an aqueous composition and so the concentrate of water-insoluble active ingredient must be stable and must be capable of easy distribution into water.

One common type is a wettable powder in which powdered insoluble material has been treated to render it wettable, but there is increasing concern about dusting and other environmental problems associated with traditional wettable powders.

Another type is a dispersible paste or cream, usually referred to as a "flowable". This can readily be diluted with water and is reasonably satisfactory for many active ingredients. However a problem with both flowables and wettable powders is that the active ingredient has to be produced in the form of particles of a desired small size and this can be difficult or impossible with some materials, especially some agrochemicals. For instance these formulations are not appropriate when the active ingredient is a liquid or when it is a relatively low melting solid, for instance a solid that melts at below 80° C., because of the difficulty of making the active ingredient in this fine particulate form.

Water insoluble liquids and low melting solids can be formulated as emulsifiable concentrates but it is now frequently considered desirable to avoid this type of formulation for environmental reasons associated with, for instance, the organic solvent that is generally present in such concentrates.

It would therefore be desirable to be able to provide an active ingredient in the form of a particulate composition which is readily dilutable by water, is substantially free of organic solvent or dusting problems, and gives a satisfactory rate of release of the active ingredient.

It is already well known to use polymeric materials in the formulation of various active ingredients. Thus it is known to diffuse a low melting or liquid active ingredient into a preformed polymeric matrix (e.g., as in U.S. Pat. No. 4,303,642) or to encapsulate an active ingredient in beads by forming an emulsion or dispersion in water of polymerisable material and the active ingredient and then polymerising the polymerisable material. The product will, depending upon the materials and process conditions, be in the form of either a particulate matrix throughout which the active ingredient is distributed or small (or large) capsules comprising a shell of polymeric material around a core containing the active ingredient.

Although these diffusion and polymerisation techniques are useful in some instances, they are relatively expensive and this is justified only because they are designed primarily to provide controlled release of an active ingredient. They are not appropriate to the more fundamental problem of providing an improved way of formulating a wide range of water insoluble agrochemical or other active ingredients in an economic manner in the form of environmentally satisfactory concentrates that can readily be diluted with water to form sprayable compositions.

There are, of course, numerous other ways of making capsules containing active ingredients.

In GB 1,275,712, an active ingredient is dispersed (as an aqueous solution or as a hydrophilic or hydrophobic powder) into a solution of a polymer in an organic solvent, the resultant dispersion is distributed into an aqueous electrolyte and the organic solvent is evaporated to cause deposition of the polymer around the initial particles of powder or aqueous solution. The capsule wall is formed by insolubilisation of the dissolved polymer and surrounds a core consisting of the powder or aqueous solution. The capsules are said to have a size of 20 $\mu$m to 5 mm and are recovered as powder.

Instead of forming a capsule wall by polymerisation or by precipitation of a polymer due to evaporation of its solvent, it is also known to form capsule walls by coacervation. Often at least two water soluble coacervating polymers are blended in aqueous solution, the polymers and their conditions of blending being such that they form a coacervate that comes out of solution to form a coating around a core consisting of one or more particles dispersed in the solution.

In GB 1,475,229 a process is described in which microcapsules are formed by dispersing an active ingredient, as a solid or a solution in high boiling (or low boiling) organic solvent, into an aqueous solution of a hydrophilic colloid, enclosing the dispersed particles within a polymeric coating formed by coacervation as a result of the addition of a second coacervating polymer solution, and then cross linking the resultant coating. The resultant microcapsules can have a wide range of particle sizes, namely 0.5 to 500 $\mu$m. In practice the capsules are separated to form a powder.

Each of GB 1,275,712 and 1,475,229 describe the incorporation of a wide range of materials as the active ingredients and included amongst the listed active ingredients are agrochemicals such as pesticides. However in practice techniques such as these do not seem to have been used successfully commercially for the formulation of agriculturally useful active ingredients and instead such methods appear to have been used primarily for encapsulating liquid inks. Numerous other coacervation techniques are described, nearly always with the primary intention of producing and recovering ink capsules that can be applied to paper.

A problem in all coacervation processes is the production of a dispersion of the material that is to be encapsulated (generally the ink) that is sufficiently stable during the coacervation proces. Once the coacervation has occurred, it is usually necessary for the encapsulated particles to be further stabilised by wall building using in situ cross linking processes. Methods in which the ink dispersion is stabilised during the coacervation technique by reliance upon polymers that go into the coavervate are described in GB 1,507,739, GB 2,073,132 and DE 3,545,803. Although these processes go through an intermediate stage in which the coacervating polymer contributes to the stability of the ink dispersion, the overall process generally involves conventional cross linking and other wall-building polymerisation processes after the initial coacervation.

Accordingly none of these proposals address or solve the problem of providing a composition of a water insoluble agrochemical or other active ingredient which requires no further polymerisation to stabilise the emulsion and which can readily be diluted, and which is stable during storage.

Another problem with coacervating techniques is that they are of rather limited applicability due to the restrictions imposed by the physical state of the active ingredient that is to be encapsulated. A method is published in WO89/04714 (after the priority date of this application) for encapsulating low melting materials but there are other materials where this, and other known methods of coacervation, are inappropriate.

Another problem with coacervating techniques is that it can be difficult with many active ingredients to obtain microcapsules that are sufficiently small to form easily a stable dilutable dispersion in water.

Another problem is that the particles that are formed containing the active ingredient are found on storage to have lost some of their activity. This appears to be a particular problem with some active ingredients that are solidified within the core after the formation of the coacervate shell.

In one aspect of the invention an agricultural or other composition is formed that comprises particles that each comprise a core enclosed within a polymeric coacervate shell formed from at least two coacervating polymers, in which the core is selected from fluid cores and solid, non-crystalline, glass cores and comprises a water insoluble agrochemical or other active ingredient.

This aspect of the invention is of particular value when applied to the encapsulation of agrochemicals (or other active ingredients) that can crystallise, since the invention holds the active ingredient in the core either in fluid form or as a solid, non-crystalline, glass form. Thus in the invention the active ingredient preferably is crystallisable and is in fluid form during coacervation, but does not subsequently crystallise within the shell. This seems to be desirable as the step of crystallisation appears to tend to disrupt the shell, and thus reduce the stability of the final product.

If the active ingredient is a crystallisable solid, it can be held in fluid form as a result of the core being in the form of a solution of the active ingredient in a solvent. In one process this solvent is retained in the particles so as to maintain the core fluid. For this purpose the solvent is preferably less volatile than water, so as to facilitate its retention in the core, and is used in an amount sufficient to maintain the core in fluid form at the end of the process. This fluid form may be a solution of the active ingredient in the solvent or it may be a melt whose melting point is held below ambient temperature as a result of the presence of the solvent. Suitable solvents for this purpose are aromatic hydrocarbons or other non-volatile solvents. The amount of the solvent is often 0.1 to 1.5, frequently 0.2 to 0.5, parts per part by weight active ingredient. The amount of solvent is preferably less than the amount of active ingredient.

The use of a non-volatile solvent is of particular value in the coacervation of trifluoralin.

Instead of forming the dispersion from a liquid composition of the active ingredient in a non-volatile solvent, it may be formed in a volatile solvent and this solvent may be evaporated by distilling the dispersion, thereby solidifying the core. Alternatively the dispersion formation may be conducted while the active ingredient is molten.

We find that it is particularly preferred that the core should not crystallise during any solidification stage involved in the formation of the product after coacervation, i.e., the solid core should have a glass structure. It seems that if the core crystallises this imposes strains and distortions on the coacervate shell leading to loss of stability on storage, but if the core solidifies as a glass then it conforms to the coacervate shell and does not destabilise it. Some molten active ingredients and solutions of active ingredients in solvent will solidify as a glass but many of the relevant active ingredients have a tendency to crystallise when being solidified from a melt or solution. Crystallisation can be prevented, and a glass structure achieved, by inclusion of sufficient of a matrix polymer in the core. The matrix polymer may be formed by polymerisation of polymerisable materials from solution within the core but preferably the core is initially formed as a solution of the matrix polymer and active ingredient in a solvent, and the solvent is evaporated by distillation of the dispersion so as to solidify the matrix polymer. If the amount of matrix polymer is insufficient, the core will crystallise but simple experimentation can be conducted to determine the minimum amount of matrix polymer that needs to be present in the core to prevent crystallisation. Generally the amount of matrix polymer needs to be at least 20%, and often at least 50%, by weight of the mixture of the matrix polymer and active ingredient.

The particles can be relatively large but are preferably substantially all below 100 $\mu$m. For instance they may be from 10 to 100 $\mu$m, often around 20 to 50 $\mu$m, and may then be used as powders. For instance powdered insecticides that are to be dusted may have a size of around 30 $\mu$m and may be used for, for instance, cockroach control. However it is particularly preferred that the particles should be below 10 $\mu$m and should be present as a dispersion in water.

In another aspect of the invention, the aqueous composition which has substantially all the particles below 10 $\mu$m in size is made by providing a first aqueous solution of a first water soluble coacervating polymer, providing a second aqueous solution of a second water soluble coacervating polymer that can interact with the first polymer to form the coacervate upon mixing the first and second solutions to form a mixed solution, mixing the said first and second solutions to form the mixed solution, providing a water immiscible, fluid, phase into the active ingredient, emulsifying this fluid phase into the mixed solution in the presence of an oil-in-water emulsifier and allowing the first and second polymers to interact and thereby coat the emulsified particles of the fluid phase to form the said polymer coacervate shell around the fluid particles, wherein the coacervate particles have 90% (by weight) below 5 $\mu$m and preferably below 2 μm. By the invention it is easily possible to obtain a composition in which 90% of the coacervated particles are below 2 μm with 50% less than 1 μm, and preferably 90% of the particles are less than 1 μm, preferably with 50% of the particles being less than 0.7 μm.

The emulsifier is conveniently an anionic emulsifier, a non-ionic emulsifier or a blend of the two. A suitable material is sold under the trade name Tensiofix B7146. The amount of emulsifier typically is from 1 to 10% of active emulsifier based on the total weight of the dispersion of aqueous medium and emulsified liquid particles.

A preferred feature of the invention is that the polymeric shell formed by coacervation can stabilise the particles against agglomeration in the aqueous medium, and so this greatly facilitates the formation of a stable dispersion of the particles in water.

Accordingly, in another aspect of the invention, a composition according to the invention is dilutable with water to form a sprayable composition and comprises a substantially stable dispersion in an aqueous medium of particles that are substantially all below 10 μm in size and that comprise a core containing a water insoluble active ingredient surrounded by a shell that has been formed by coacervation from at least two water soluble coacervating polymers and that stabilises the particles against agglomeration in the aqueous medium.

Thus in the invention the coacervating shell is a material that promotes the stability of the particles, as a result of which the coacervated particles have less tendency to settle out and agglomerate than would similarly sized particles of the active ingredient alone, in an otherwise identical aqueous medium. Thus, for the first time, the final product relies upon the coacervate shell to promote the stability of the final product that is to be stored and transported to the point of use, where it can be converted into a novel sprayable composition merely by dilution with water. This is therefore in contrast to processes such as those described in GB 1,507,739 where some initial stabilisation is achieved but the process that is conducted involves further reaction of the coacervate shell so as to form a relatively unstable dispersion from which the capsules could be separated relatively easily.

The concentrated composition of the invention must be sufficiently stable that it either remains as a true dispersion during storage or, if settlement does occur, can easily be redispersed merely by stirring. The composition may include additional emulsifiers, dispersants or dispersion stabilisers, but preferably the amount of such materials is very much less, below half and preferably below one quarter, the amount that would be required to stabilise the dispersion in the absence of the stabilising coacervate shell. Preferably the composition is substantially entirely free of such materials although coacervating polymer is preferably dissolved in the solution. Thus the coacervating shell may provide most, and preferably all, of the stabilising properties that are required.

The coacervate shell can be made by bringing the polymers out of solution by, for instance, mixing counterionic polymers that cause mutual insolubilisation either in the presence of dispersed active ingredient or with the subsequent addition of it. Such techniques are known from, for instance, GB 2,073,132.

In order that the coacervating shell can provide these properties it is desirable for the shell to be ionically charged, so that the particles then repel one another as a result of the like ionic charges on them. Preferably the particles have a relatively high positive or, preferably, negative zeta potential. Thus the zeta potential is preferably greater than −30 mv, and often greater than −50 mv, for instance the zeta potential can be as high as −100 mv or even higher. This can be achieved by using sufficient amounts of an ionically charged polymer that the ionic charges in the polymer impart the desired zeta potential to the particles, and preferably excess of the ionic polymer is dissolved in the aqueous medium, thus promoting mutual repulsion of the particles. Thus preferably one of the coacervating polymers is anionic and the amounts of polymers that are used are such that the particles are rendered anionic and the aqueous medium has some of the anionic polymer in solution in it. The ionically charged polymer should contain a sufficiently high proportion of ionic groups to impart the desired ionic charge to the particles.

The ionic polymer that contributes to the charge of the particles needs to be relatively hydrophilic in order that it gives good dispersing properties but this conflicts with the requirement that it shall come out of solution as a coacervate coating. A preferred way of insolubilising the anionic polymer so as to form a coacervate while still leaving the polymer with hydrophilic properties, is to coacervate it with a non-ionic or, preferably, cationic polymer that has characteristics such that it can interact with the anionic polymer to form the coacervate around the hydrophobic active ingredient but without destroying the dispersing properties of the anionic polymer shell. Preferably the cationic polymer has a lower molecular weight than the anionic polymer and the anionic polymer should be present in a molar excess, that is to say there should be a significantly larger number of anionic groups than cationic groups.

In order that the anionic polymer is hydrophilic, it is preferred to make it from a water soluble ethylenically unsaturated monomer or monomer blend that includes carboxylic or other anionic monomer. Preferably a 20:80 to 80:20 blend of acrylamide and (meth) acrylic acid (usually as sodium salt) is used. The lower molecular weight cationic polymer can be made from water soluble ethylenically unsaturated monomer or monomer blend that includes cationic polymer, a condensation polymer, most preferably a cationised urea formaldehyde or melamine formaldehyde polymer.

Suitable blends of molecular weight can be identified by experimentation, but generally the cationic polymer should have a molecular weight of below 100,000 and in practice the molecular weight should normally be below 50,000 and often below 10,000, while the anionic polymer will normally have a molecular weight above 100,000 and in practice often above 200,000, and up to 1 to 2 million although higher molecular weights can sometimes be used. At least one of the polymers (generally the anionic) can be amphoteric provided this does not prevent the desired formation of a stabilising coacervate.

What seems to be happening is that several molecules of cationic polymer become ionically bonded to parts of an anionic polymer chain so as to render those parts where charge neutralisation occurs more hydrophobic, thus attracting those parts to the hydrophobic active ingredient. The remainder of the anionic polymeric chain remains hydrophilic, thus promoting a high negative zeta potential and good stabilisation properties in an aqueous medium that includes an aqueous solution of the anionic polymer or of some other similar anionic polymer.

Suitable polymeric materials are described in, for instance, DE-A-3,545,803, GB 2,073,132, and 1,507,739 and U.S. Pat. No. 4,100,103.

The coacervate polymeric coating generally provides at least 10% and often at least 20% by weight of the dry weight of the particles but it is usually unnecessary for it to provide more than 50%, and usually it provides less than 40% of the dry weight of the particles. The content of active ingredient in the aqueous concentrate typically is in the range 5 to 20% by weight based on the concentrate.

In the aqueous dispersions of the invention, at least 90% by weight of the particles should be below about 10 $\mu$m in size since it will be very difficult to achieve adequate stabilisation if a significant proportion of the particles are above about 10 $\mu$m, and preferably at least 95% by weight are below 10 $\mu$m. Preferably at least 90, and usually at least 95%, by weight are below 5 $\mu$m. At least 50% are preferably below 3 $\mu$m. The coacervation is preferably conducted so as to make particles that initially have this size, but if necessary the coacervated material can be stirred or milled so as to break agglomerates down to the desired particle size.

The active ingredient can be any material that it is desired to provide in particulate form. Preferably it is an agriculturally useful material such as a semiochemical, nutrient or plant growth regulator or, preferably, a herbicide or pesticide. Suitable pesticides include insecticides, fungicides, nematocides, and biocides. Other suitable active ingredients that can usefully be incorporated into the particulate compositions of the invention include, for instance, perfumes, fragrances, pharmaceuticals and veterinary materials. Preferred active ingredients are chlorpyriphos, chlorpyriphos methyl, and trifluralin.

Although the invention is primarily of value for the production of agrochemical compositions that are stable dispersions that can be diluted with water, it is possible to apply the same coacervation technique to the production of other agrochemical particulate compositions.

Accordingly, another aspect of the invention is directed to a composition that comprises particles that comprise a core comprising a water insoluble agrochemical surrounded by a shell that has been formed by coacervation as described above, preferably by means of a low molecular weight water soluble cationic polymer with a molar excess of a higher molecular weight water soluble anionic polymer. These compositions can be, for instance, powders obtained by separating the coacervated particles from the described aqueous dispersion, followed by drying. The resultant powders can be used as such or can be made into granules or other larger particles, and will have the advantage that they will be readily dispersible into water.

In order to perform the coacervation process it is necessary to provide a dispersion of the active ingredient in the desired particulate form, and conventional methods of providing such a dispersion, and conducting the coacervation, tend to be unsatisfactory with many of the agrochemicals and other active ingredients with which we are preferably concerned, even though the methods may be satisfactory for inks. Accordingly we have developed two methods of particular value in the invention.

When the active ingredient is a solid that melts at below 80° C. (often below 50° C.), the process preferably comprises melting the active ingredient, dispersing it into the aqueous medium at a temperature at which it remains molten and under conditions to generate particles of the desired size (substantially all below 10 $\mu$m), coating the resultant dispersed particles by the coacervation process, and cooling the particles. This cooling may occur before the coacervation but after the dispersion stage, but often occurs during or, preferably, after the coacervation. After cooling, the particles are at a temperature below the melting point of the active ingredient.

Another convenient way of performing the process on many agrochemicals and other suitable active ingredients comprises dispersing the active ingredient into the aqueous medium while the active ingredient is present as a solution in an organic solvent that is more volatile than water, and thereby forming particles substantially all below 10 $\mu$m. The dispersed particles are then coated by the coacervation step while dispersed in the aqueous medium, and the resultant dispersion is then distilled to remove the organic solvent. If the active ingredient is crystallisable then it is preferred that polymeric matrix or other material is included in the core with the active ingredient to prevent crystallisation when sufficient of the volatile solvent has been evaporated that crystallisation would otherwise have occurred. For instance some non-volatile solvent can be included to hold the material in solution, or polymeric matrix may be included in an amount sufficient to prevent crystallisation.

This technique of coacervating around a solution in volatile solvent and then distilling off the volatile solvent is of general applicability to the production of a wide range of active ingredients and so, according to another aspect of the invention a process for making a particulate composition comprises dispersing into an aqueous medium a solution of water insoluble active ingredient dissolved in an organic solvent that is more volatile than water, coating the resultant dispersed particles by coacervation of at least two water soluble coacervating polymers and thereby stabilising the particles against agglomeration while dispersed in the aqueous medium, and distilling the dispersion to remove the organic solvent.

It is possible to make relatively coarse particles, e.g., having an average size above 10 $\mu$m typically in the range 50 to 500 $\mu$m or even larger, by appropriate optimisation of the content of the aqueous solution and the manner of dispersing the organic solution of active ingredient into the aqueous solution. It is possible to separate these coarse particles from the aqueous medium in conventional manner and thus to form a dry particulate powder. Generally however the process results in the production of an aqueous dispersion as discussed above.

In this process, the active ingredient can be a liquid at room temperature (20° C.) but is generally a solid. It should be soluble in one or more organic solvents. The solution in the organic solvent is preferably a true solution but it can be a partial solution, for instance being a dispersion that is stable in the absence of a dispersion stabiliser. The solubility of the active ingredient in the chosen solvent can be high or low, provided that it is not so low that it is impossible to achieve a solution of useful concentration.

The solvent that is used should be substantially water-immiscible in order that it will emulsify or disperse (rather than dissolve) into the aqueous medium. The dispersion can be achieved by mixing the solution into the aqueous medium under shear using, for instance, a Silverson mixer or other suitable emulsifier or homogeniser apparatus.

The solvent should be significantly more volatile than water and should have a boiling point substantially below the boiling point of water. For instance the solvent preferably has a boiling point below 70° C. and preferably between room temperature and 50° C. (at atmospheric pressure). Preferably the solvent forms an azeotrope with water so that the removal of solvent by distillation involves azeotropic distillation of substantially all the solvent with part only of the water of the aqueous medium.

Suitable solvents include any of the relatively low boiling water-immiscible organic solvents. The solvent is normally a hydrocarbon or halogenated hydrocarbon, the hydrocarbon generally being aliphatic or cycloaliphatic. Methylene chloride is particularly preferred.

Generally the coacervate coating is substantially complete before the product is distilled, but in some instances it can be desirable to rely upon the heating (that is supplied to cause distillation) also causing or completing the coacervation process.

The evaporation can be conducted by distillation at atmospheric or reduced pressure and is generally conducted as an azeotropic distillation. This is generally conducted under reduced pressure. By appropriate selection of the solvent and the pressure at which distillation is conducted it is possible to effect the distillation at low temperatures, e.g., as low as 50° C. or even as low as 30° C., and this is very advantageous if the active ingredient is sensitive to elevated temperatures, for instance being thermally unstable or volatile.

The distillation is preferably continued until the amount of solvent remaining is so low that the resultant composition, even after storage in a closed container, does not have a measurable flash point. Even if some solvent does remain (e.g., 2-30% based on active ingredient and total polymer) the amount is preferably as low as possible so as to maximise the solids content of the composition and to minimise environmental problems due to the solvent.

When, as is often preferred, the final product is to be an aqueous dispersion, the distillation conditions must, of course, be such as to remove the solvent whilst allowing sufficient of the aqueous phase to remain. Generally the amount of water in the distilled product is at least 30% and often at least 50%. Solids contents in the range 20% to 60% are suitable.

The coacervate shell can be a discontinuous stabilising shell, for instance a particulate shell of the type formed in DE 3,545,803, but preferably the shell is a substantially continuous polymeric coating. We have found that the polymeric coating formed by coacervation does not provide a serious impediment to satisfactory rates of release of the active ingredient to the pest or plant where the desired effect is to be achieved. However in some instances it is desirable to modify the capsules so as to regulate the rate of release.

Whereas it is preferred, from the stabilisation point of view, that the shell of the polymer particles in the dispersion should be the unreacted shell formed by coacervation, it can be desirable to subject the polymer in the shell to further reaction, provided this does not seriously impair the stabilisation properties of the shell. Thus although the shell preferably contains all the unreacted anionic groups initially present at the end of the coacervation process, if desired some of these can be further reacted so as to modify the properties of the shell. For instance they can be subjected to cross-linking with further urea formaldehyde or melamine formaldehyde resin as described in GB 1,507,739 or 2,073,132. This will increase the strength of the shell but will reduce the stability of the dispersion and a better way of controlling the rate of release is for the core of the particles to comprise a polymeric matrix through which the active ingredient is distributed. The polymeric matrix should be water insoluble.

According to a another aspect of the invention, a particulate composition comprises particles having a core and a polymeric coating formed by coacervation from at least two water soluble coacervating polymers, and the core comprises a water-insoluble matrix polymeric material and a water-insoluble active ingredient. Preferably the particles are below 10 μm in size, as discussed above, and the composition is a stable dispersion in water. The active ingredient may be distributed substantially throughout the matrix either as a dispersion or solution in the polymer.

Although the composition can be made by coacervation around, for instance, pre-formed solid particles of the core, it is, as explained above, preferred to form the polymeric coacervate coating around fluid particles. It is possible for the core to remain in the fluid state and this is preferred when the active ingredient is crystallisable. However sometimes it is preferred that the core should be in solid form and should be substantially free of organic solvent, and it is then preferred for the active ingredient to be distributed throughout a solid polymeric matrix that is present in an amount sufficient to prevent crystallisation.

Preferably the active ingredient and any matrix polymeric material (or material that is a precursor of that) are both soluble in an organic solvent that is more volatile than water and the dispersion is made by the solvent process described above. In this type of process, the polymer can be one that is, for instance, a dispersion that is stable in the absence of a dispersion stabiliser in the chosen solvent for the active ingredient or can be a polymeric material that has been formed by reaction in the particles from precursor material that is soluble in the chosen solvent, i.e., the precursor for the matrix polymer must be soluble in the solvent.

When the particles are being made by the melting technique described above then the matrix polymer must be molten at the chosen temperature or must be made from a precursing material that will polymerise during or after dispersing the particles in the aqueous medium.

It is often desirable to make the matrix polymer particles by dispersing precursor, polymerisable material and the active ingredient in the aqueous medium and then causing polymerisation or cross linking.

The precursor material can be monomeric or other low molecular weight material but is preferably polymeric. Thus the reaction of the precursor polymer to form the matrix polymer may be, for instance, cross linking or graft polymerisation. When the solvent process is used, the matrix polymer in the final particles is preferably substantially unchanged chemically from the polymer that is dissolved into the initial solution of active ingredient and organic solvent.

The matrix polymer is normally selected such that the core is not only insoluble in the aqueous medium but is also substantially unswollen by the aqueous medium. Suitable polymers are any of the vinyl (or allyl) addition polymers that can conveniently be made by oil-in-water polymerisation or solution polymerisation in an organic solvent of ethylenically unsaturated monomer or monomer blend that is insoluble in water. Preferred polymers are acrylic polymers formed from monomers that comprise alkyl (meth) acrylate, generally in an amount of 30 to 100%. Other monomers that can be included, generally in amounts of less than 70% and preferably less than 40%, include styrenes, acrylonitrile, vinyl halides and the other relatively hydrophobic monomers that conventionally can be included in acrylic oil-in-water emulsion polymerisation. The polymer is generally linear but chain branching or slight cross linking can sometimes be desirable and so cross linking agent may be included.

The preferred matrix polymer is formed from 50 to 100% (preferably 80 to 100%) alkyl (meth) acrylate, and 0 to 50% styrene. Percentages are by weight. The alkyl group generally contains 1 to 10, preferably 2 to 6, carbon atoms. Blends of alkyl (meth) acrylates may be used. Polymers of 80 to 100% isobutyl methacrylate are particularly suitable.

Preferably the matrix polymer has a glass transition point (Tg) of above $-20°$ C. and generally above $-5°$ C. It is normally preferred for the glass transition point to be below 100° C. and usually below 40° C. By appropriate choice of Tg, monomers, and the ratio by weight of polymer:active ingredient, it is possible to regulate the rate of release.

Preferably the matrix polymer is substantially non-ionic and preferably it is formed entirely from non-ionic material. This is desirable since it facilitates the performance of the manufacturing process and in particular it minimises the risk of undesirable interaction between the matrix polymer and the coacervating polymers. Thus the polymeric matrix should be substantially non-swelling in the aqueous medium, and chemically inert to the coacervating polymers. However it can be convenient for it to swell slightly when the pH is changed, for instance when it is introduced into a more alkaline environment than the aqueous medium in which it is formed. Thus the matrix polymer may include (meth) acrylic or other acid groups and may be in the substantially free acid and non-swollen form in the aqueous medium but may swell slightly when exposed to alkaline conditions, such as may exist in the soil or on a plant leaf, due to ionisation of the carboxylic groups.

Since the matrix polymer (or its precursor) and active ingredient initially are both dissolved in the same solution, they are present in intimate admixture in the final particles and the polymer provides a matrix for the active ingredient.

When polymeric matrix is present, it is generally present in an amount of at least 0.2 part, preferably at least 0.5 part, per part dry weight of active ingredient, but it is usually unnecessary for it to provide more than about 2, or at the most about 5, parts by weight of the active ingredient.

The aqueous concentrates of the invention can include conventional additives to improve the stability of the composition (for instance thickeners such as gums or other natural polymers or synthetic polymeric thickeners). It may include dispersants and/or wetters to facilitate its dilution to form a sprayable composition and to facilitate its subsequent spraying and adherence to plants, soil or other substrate to which it is sprayed.

An advantage of the aqueous dispersions of the invention, is that a flowable agrochemical composition, containing particles of a second agrochemical active ingredient, can be blended into the composition. Thus it is possible for the first time to provide in a convenient and environmentally acceptable form a concentrate of two insoluble agrochemicals wherein at least one has physical properties such that it cannot be put into the form of a conventional flowable.

Instead of using the aqueous dispersion as a concentrate for forming a dilute agricultural spray, it can be used for other purposes. For instance the concentrate (or a diluted composition formed from it) maybe applied by spraying or otherwise on to a granular or other carrier, for instance to make a dry particulate composition that can be spread as a dry powder. Another way of making a spreadable powder is by aggregating the particles of the dispersion and then drying the aggregates. These aggregates can then be spread as dry powder or can be dispersed into water, whereupon the aggregates will disintegrate.

The following are some examples.

EXAMPLE 1

Preparation of an Aqueous Dispersion of Chlorpyrifos 120 g of a 100% polyisobutyl acrylate (as matrix polymer) and 120 g Chloropyrifos technical grade were dissolved in 520 g dichloromethane, to form Solution A.

168 g of a 20% solution of a copolymer of acrylamide/sodium acrylate having molecular weight about 400,000 were dissolved in 600 g water (Solution B).

76 g of a 35% cationic urea/formaldehyde resin containing about 10 urea units and sold under the trade name BC777 was dissolved in 100 g water (Solution C).

Solution B was subjected to stirring by a Silverson stirrer. Solution C was added over 20 secs., stirring was continued for 30 secs., and then solution A was added over 30 secs. Stirring was continued for a further 40 secs., and defoamer was added. A white emulsion was obtained.

The stirred emulsion was subjected to distillation under reduced pressure at a maximum temperature of 45° C., until all the dichlormethane was removed.

After sieving through a nylon mesh, a stable aqueous dispersion of solid particles was obtained and had a solids content of 26.5% by weight. The Chlorpyrifos content of the product was 10.1% and the median particle size was 2.21 $\mu$m. The zeta potential of the dispersion was $-110.4$ mv.

The dispersion was stable on storage, and was diluted with water to give a 0.3% concentration of particles in the sprayable solution. Some pot-grown cauliflowers were sprayed with the solution while others (the controls) were left untreated. Some of the treated and controlled pots were inoculated with cabbage root fly eggs immediately while others were inoculated after 5, 10, 15 or 22 weeks, and the pots were then grown in an insectary whilst the cabbage root fly larvae pupated. The mean numbers of larvae and pupae in each pot were counted. The results were as follows.

|  | Week | | | | |
|---|---|---|---|---|---|
|  | 0 | 5 | 10 | 15 | 22 |
| Control-number | 5.0 | 9.6 | 5.4 | 5.7 | 0.3 |
| Sample-number | 0 | 0 | 0.1 | 0 | 0 |

This demonstrates that the active ingredient was effective both immediately and for a period of 22 weeks, the maximum useful life of the crop.

EXAMPLES 2, 3 AND 4

The process was repeated in a manner similar to Example 1 but varying amounts of matrix polymer: 0 g, 60 g, 240 g were added. In each case a reasonably stable dispersion was obtained. However the stability of Examples 3 and 4 was significantly higher than the stability of Example 2 and this is attributed to the fact that Example 2 contains no matrix polymer and the active ingredient is in crystalline form in the core, whereas in Example 3 (50% polymer matrix based on active ingredient) and Example 4 the polymer matrix is present in an amount sufficient to prevent the active ingredient forming a crystal within the core. Since the core is a non-crystalline solid it can conveniently be referred to as a glass.

EXAMPLE 5

Preparation of an Aqueous Dispersion of 1,7-Dioxaspiro (5,5) Undecane ('Spiroketal')

Spiroketal is the principle component of the sex pheromone of the Olive fly: Dacus oleae.

160 g of a 95:5 copolymer of methyl methacrylate: ethyl acrylate and 22.5 g Spiroketal were dissolved in 640 g dichlormethane to form Solution A.

Solution B and C were prepared as in Example 1.

The solutions A, B and C were mixed in a manner identical to Example 1.

The dichloromethane was removed by distillation under reduced pressure in the temperature range 40°-50° C.

The final product was a stable dispersion of white particles of <5 $\mu$m size.

EXAMPLE 6

This was identical to Example 5, except that the polyisobutyl acrylate of Example 1 was used in place of the 95:5 copolymer.

It was found that the rate of release of the spiroketal to the atmosphere was different in the two products.

EXAMPLE 7

Solutions B and C were made and mixed as in Example 1, and the mixed solution was then heated to 45° C. and 800 g molten Trifluralin (technical grade) was added at 45° C. and blended using a Silvercon stirrer. The liquid was allowed to cool with gentle sitrring and was then subjected to stirring with a Silversen stirrer until 90% of the particles were below 10 $\mu$m and 50% were below 5 $\mu$m. The product was a stable orange suspension containing 45% by weight Trifluralin.

EXAMPLE 8

A conventional flowable containing 50% by weight Linuron was made by bead milling a mixture of 538 g Linuron (technical grade) 253 g water, 138 g monoothylono glycol, 69 g surfactant and 1 g antifoam, until the particle size of the flowable was 100% below 10 $\mu$m.

150 g of this flowable suspension was then mixed with 333 g of the Trifluralin suspension of Example 7 and 76 g water to give a stable suspension containing 300 g/l Trifluralin and 150 g/l Linuron.

EXAMPLE 9

A 3:1 mixture of Trifluralin:Shellsol A was found to form a stable solution at R.T.

The above solution was found to emulsify in water when mixed with the surfactant *Tensiofix B7416.

(*The Tensiofix product is a blend of anionic and non-ionic surfactants).

Solution A was formed by adding to 356.25 g molten Trifluralin (technical); 118.75 g Shellsol A, and 125 g Tensiofix B7416 and cooled to room temperature.

63 g of a 20% solution of a copolymer of acrylamide/sodium acrylate having M.W. $\simeq$ 400,000 was dissolved in 300 g water (Solution B).

38 g of a 35% cationic urea/formaldehyde resin containing about 10 urea units; sold under the trade name BC 777, was dissolved in 50 g water (Solution C).

Solution B was subjected to stirring by a Silverson stirrer. Solution C was added over 10 secs, stirring was continued for 15 seconds and then Solution A was added over 15 seconds. Stirring was continued over another 50 seconds.

The final product contained 35% Trifluralin and was stable for a minimum of 2 weeks at 54° C. 90% of the particles were less than 1 $\mu$m.

EXAMPLE 10

The preparation of the trifluralin product was carried out in exactly the same manner as in Example 9, except that the Tensiofix surfactant was omitted from Solution A.

The product in this case had 90% of the particles less than 10 $\mu$m with 50% less than 5 $\mu$m.

The stability of the product in Example 9 is much higher than the stability of the product in Example 10.

We claim:

1. An agricultural composition that comprises particles that are substantially all below 100 $\mu$m in size and that each comprise a core enclosed within a polymeric coacervate shell formed from at least two coacervating polymers, in which the core is a solid, non-crystalline, core comprising a polymeric matrix containing a crystallizable water insoluble agrochemical selected from the group consisting of herbicides, pesticides, semiochemicals, plant growth regulators and nutrients and the amount of polymeric matrix is at least 20% by weight based on the weight of agrochemical and such that crystallization of the agrochemical in the core is substantially prevented.

2. A composition according to claim 1 in the form of a powder.

3. An agricultural composition that is an aqueous concentrate that is dilutable with water to form a sprayable composition that comprises a substantially stable dispersion in an aqueous medium of particles that are substantially all below 10 $\mu$m in size and that each comprise a core enclosed within a polymeric coacervate shell formed from at least two coacervate polymers, in which the core is a solid, non-crystalline, core comprising a polymeric matrix containing a crystallizable water insoluble agrochemical selected from the group consisting of herbicides, semiochemicals, pesticides, plant growth regulators and nutrients and the amount of polymeric matrix is at least 20% by weight based on the weight of agrochemical and such that crystallization of the agrochemical in the core is substantially prevented.

4. A composition according to claim 3 in which the active ingredient is trifluoralin.

5. A composition according to claim 3 in which the active ingredient is crystallisable and the core comprises a polymeric matrix containing the active ingredient and the amount of polymeric matrix is at least 50% by weight based on the weight of active ingredient, whereby crystallisation of the active ingredient in the core is substantially prevented.

6. A composition according to claim 3 and that has been made by providing a first aqueous solution of a first water soluble coacervating polymer, providing a second aqueous solution of a second water soluble coacervating polymer that can interact with the said first coacervating polymer to form a coacervate upon mixing the said first and second solutions, providing a water immiscible fluid phase comprising the agrochemical, mixing the said first and second solutions and emulsifying the said fluid phase in the mixed solution in the presence of oil-in-water emulsifier and allowing the polymers to interact and thereby to coat the emulsified particles by coacervation to cause the said polymeric shell, wherein at least 90% by weight of the coacervate particles have a size below 2 μm.

7. A composition according to claim 3 wherein the coacervate coating stabilises the particles against agglomeration in the aqueous medium.

8. A composition according to claim 6 in which the water immiscible fluid phase comprises a solution of the active ingredient in an organic solvent.

9. An agricultural concentrate composition that is dilutable with water to form a sprayable composition and that comprises a substantially stable dispersion in an aqueous medium of particles that are substantially all below 10 μm in size and that comprise a core enclosed within a polymer coacervate shell, in which the core contains a water insoluble agrochemical that is selected from the group consisting of pesticides, herbicides, plant growth regulators, nutrients and semiochemicals, and the composition has been made by providing a first aqueous solution of a first water soluble coacervating polymer, providing a second aqueous solution of a second water soluble coacervating polymer that can interact with the said first coacervating polymer to form the coacervate upon mixing the first and second solutions to form a mixed solution, mixing the said first and second solutions and forming a dispersion of particles substantially all below 10 μm in size of the agrochemical in the said mixed solution and allowing the first and second polymers to interact and thereby coat the dispersed particles by coacervation to form the said polymer coacervate shell, and wherein the said polymeric coacervate shell stabilizes the particles against agglomeration in the aqueous medium, and in which the second coacervating polymer is cationic urea formaldehyde or cationic melamine formaldehyde having a molecular weight of below 100,000 and the first coacervating polymer is an anionic polymer of ethylenically unsaturated carboxylic acid having a molecular weight above 100,000.

10. A composition according to claim 9, in which the agrochemical is selected from the group consisting of, chloropyrophos methyl and trifluralin.

11. A composition according to claim 9 in which the core comprises a polymeric matrix through which the agrochemical is distributed.

12. A composition according to claim 9 in which the first coacervating polymer is anionic and renders the particles anionic, and the said anionic polymer is also dissolved in the said aqueous medium of the concentrate.

13. A composition according to claim 9 in which the first coacervating polymer is anionic and the second coacervating polymer is cationic and has a lower molecular weight than the first coacervating polymer and the amounts of the said firstr and second solutions that are mixed to form the said mixed solution are such that the mixed solution contains a molar excess of the higher molecular weight water soluble anionic polymer.

14. A composition according to claim 9 in which the anionic polymer is a copolymer of 20 to 80% acrylamide and 18 to 20% acrylic acid.

15. A composition according to claim 9 in which the dispersion of the particles of the agrochemical in the said mixed solution has been made by dispersing the water insoluble agrochemical as a solution dissolved in an organic solvent that is more volatile than water, and the resultant dispersion is distilled to remove the organic solvent after formation of the said polymeric shell.

16. An agricultural concentrate composition that is dilutable with water to form a sprayable composition and that comprises a substantially stable dispersion in an aqueous medium of particles that are substantially all below 10 μm in size and that comprise a core enclosed within a polymer coacervate shell, in which the core contains a water insoluble agrochemical that is selected from the group consisting of pesticides, herbicides, plant growth regulators, nutrients and semiochemicals, and the composition has been made by providing a first aqueous solution of a first water soluble coacervating polymer, providing a second aqueous solution of a second water soluble coacervating polymer that can interact with the said first coacervating polymer to form the coacervate upon mixing the first and second solutions to form a mixed solution, mixing the said first and second solutions and forming a dispersion of particles substantially all below 10 μm in size of the agrochemical in the said mixed solution and allowing the first and second polymers to interact and thereby coat the dispersed particles by coacervation to form the said polymer coacervate shell, and wherein the said polymeric coacervate shell stabilizes the particles against agglomeration in the aqueous medium, and in which the agrochemical is a solid that melts at below 80° C. and the dispersion of particles of the agrochemical in the mixed solution has been made by melting the agrochemical, dispersing it at a temperature at which it remains molten and cooling the particles before, during or after the coacervation to a temperature below the melting point of the agrochemical.

17. A composition that comprises particles that comprise a core comprising a water insoluble agrochemical surrounded by a shell that has been formed by coacervation of a low molecular weight water soluble cationic polymer with a molar excess of a higher molecular weight water soluble anionic polymer and in which the shell has been formed by coacervation of cationic urea formaldehyde or cationic melamine formaldehyde having a molecular weight of below 100,000 with a molar excess of water soluble anionic polymer of ethylenically unsaturated carboxylic acid and having molecular weight above 100,000.

18. An agricultural concentrate composition that is dilutable with water to form a sprayable composition and that comprises a substantially stable dispersion in an aqueous medium of particles that are substantially all below 10 μm in size and that comprises a core enclosed within a polymer coacervate shell, in which the core contains a water insoluble agrochemical that is selected from the group consisting of pesticides, herbicides, plant growth regulators, nutrients and semiochemicals, and the composition has been made by providing a first aqueous solution of a first water soluble coacervating polymer, providing a second aqueous solution of a second water soluble coacervating polymer that can interact with the said first coacervating polymer to form the coacervate upon mixing the first and second solutions to form a mixed solution, mixing the said first and second solutions and forming a dispersion of particles substantially all below 10 μm in size of the agrochemical in the said mixed solution and allowing the first and second polymers to interact and thereby coat the dispersed particles by coacervation to form the said polymer coacervate shell, and wherein the said polymeric coacervate shell stabilizes the particles against agglomeration in the aqueous medium, and in which the first coacervating polymer has a molecular weight above 200,000 and the second coacervating polymer has a molecular weight below 50,000.

19. An agricultural concentrate composition that is dilutable with water to form a sprayable composition and that comprises a substantially stable dispersion in an aqueous medium of particles that are substantially all below 10 μm in size and that comprise a core enclosed within a polymer coacervate shell, in which the core contains a water insoluble agrochemical that is selected from the group consisting of pesticides, herbicides, plant growth regulators, nutrients and semiochemicals, and the composition has been made by providing a first aqueous solution of a first water soluble coacervating polymer, providing a second aqueous solution of a second water soluble coacervating polymer that can interact with the said first coacervating polymer to form the coacervate upon mixing the first and second solutions to form a mixed solution, mixing the said first and second solutions and forming a dispersion of particles substantially all below 10 μm in size of the agrochemical in the said mixed solution and allowing the first and second polymers to interact and thereby coat the dispersed particles by coacervation to form the said polymer coacervate shell, and wherein the said polymeric coacervate shell stabilizes the particles against agglomeration in the aqueous medium, and in which the first coacervating polymer is an anionic polymer having a molecular weight of above 100,000 and formed of ethylenically unsaturated polymer comprising carboxylic acid and the second coacervating polymer is a cationic polymer having a molecular weight below 100,000 and selected from a group consisting of formaldehyde condensation polymers and polymers of ethylenically unsaturated monomer comprising cationic monomer.

20. An agricultural concentrate composition that is dilutable with water to form a sprayable composition and that comprises a substantially stable dispersion in an aqueous medium of particles that are substantially all below 10 μm in size and that comprise a core enclosed within a polymer coacervate shell, in which the core contains a water insoluble agrochemical that is selected from the group consisting of pesticides, herbicides, plant growth regulators, nutrients and semiochemicals, and the composition has been made by providing a first aqueous solution of a first water soluble coacervating polymer, providing a second aqueous solution of a second water soluble coacervating polymer that can interact with the said first coacervating polymer to form the coacervate upon mixing the first and second solutions to form a mixed solution, mixing the said first and second solutions and forming a dispersion of particles substantially all below 10 μm in size of the agrochemical in the said mixed solution and allowing the first and second polymers to interact and thereby coat the dispersed particles by coacervation to form the said polymer coacervate shell, and wherein the said polymeric coacervate shell stabilizes the particles against agglomeration in the aqueous medium, and in which the said polymer coacervate shell stabilizes the particles against agglomeration in the aqueous medium as a result of having a negative zeta potential that is numerically greater than −30 mv.

21. An agricultural composition that is an aqueous concentrate that is dilutable with water to form a sprayable composition that comprises a substantially stable dispersion in an aqueous medium of particles that are substantially all below 10 μm in size and that each comprise a core enclosed within a polymeric coacervate shell formed from at least two coacervate polymers, in which the core is selected from the group consisting of fluid cores and solid, non-crystalline cores comprising a polymeric matrix containing a crystallizable water insoluble agrochemical selected from the group consisting of herbicides, semiochemicals, pesticides, plant growth regulators and nutrients and in which the said polymer coacervate shell stabilizes the particles against agglomeration in the aqueous medium as a result of having a negative zeta potential that is numerically greater than --30 mv.

22. An agricultural composition that is an aqueous concentrate that is dilutable with water to form a sprayable composition that comprises a blend of (a) a substantially stable dispersion in an aqueous medium of particles that are substantially all below 10 μm in size and that each comprise a core enclosed within a polymeric coacervate shell formed from at least two coacervate polymers, in which the core is selected from the group consisting of fluid cores and solid, non-crystalline cores comprising a polymeric matrix containing a crystallizable water insoluble agrochemical selected from the group consisting of herbicides, semiochemicals, pesticides, plant growth regulators and nutrients and (b) a water dispersible paste or cream containing particles of a second agrochemical active ingredient selected from the group consisting of herbicides, seriochemicals, pesticides, plant growth regulators and nutrients.

23. A composition according to claim 1 in which the agrochemical is selected from the group consisting of chlorpyriphos, chlorpyriphos methyl and trifluralin.

24. A composition according to claim 3 in which the agrochemical is selected from the group consisting of chlorpyriphos, chlorpyriphos methyl and trifluralin.

25. A composition according to claim 16 in which the agrochemical is selected from the group consisting of chlorpyriphos, chlorpyriphos methyl and trifluralin.

26. A composition according to claim 17 in which the agrochemical is selected from the group consisting of chlorpyriphos, chlorpyriphos methyl and trifluralin.

27. A composition according to claim 18 in which the agrochemical is selected from the group consisting of chlorpyriphos, chlorpyriphos methyl and trifluralin.

28. A composition according to claim 19 in which the agrochemical is selected from the group consisting of chlorpyriphos, chlorpyriphos methyl and trifluralin.

29. A composition according to claim 20 in which the agrochemical is selected from the group consisting of chlorpyriphos, chlorpyriphos methyl and trifluralin.

30. A composition according to claim 21 in which the agrochemical is selected from the group consisting of chlorpyriphos, chlorpyriphos methyl and trifluralin.

31. A composition according to claim 17 in which the core comprises a polymeric matrix through which the agrochemical is distributed.

32. A composition according to claim 18 in which the core comprises a polymeric matrix through which the agrochemical is distributed.

33. A composition according to claim 19 in which the core comprises a polymeric matrix through which the agrochemical is distributed.

34. A composition according to claim 20 in which the core comprises a polymeric matrix through which the agrochemical is distributed.

35. A composition according to claim 21 in which the core comprises a polymeric matrix through which the agrochemical is distributed.

36. A composition according to claim 22 in which the core comprises a polymeric matrix through which the agrochemical is distributed.

37. A composition according to claim 3 which has been made by providing a solution in volatile organic solvent of the said active ingredient and the said polymeric matrix, forming a dispersion of particles substantially all below 10 $\mu$m in size of said solution in an aqueous solution of the said at least 2 coacervating polymers and thereby coating the particles by coacervation to form the said polymer coacervate shell, and distilling the dispersion to remove the said volatile organic solvent after formation of the said polymeric shell.

38. An agricultural composition that comprises particles that are substantially all below 100 $\mu$m in size and that each comprise a core enclosed within a polymeric coacervate shell formed from at least one coacervating polymer, in which the core is a solid, non-crystalline, core comprising a polymeric matrix containing a crystallizable water insoluble agrochemical selected from the group consisting of herbicides, pesticides, semiochemicals, plant growth regulators and nutrients and the amount of polymeric matrix is at least 20% by weight based on the weight of agrochemical and such that crystallization of the agrochemical in the core is substantially prevented.

39. An agricultural composition that is an aqueous concentrate that is dilutable with water to form a sprayable composition that comprises a substantially stable dispersion in an aqueous medium of particles that are substantially all below 10 $\mu$m in size and that each comprise a core enclosed within a polymeric coacervate shell formed from at least one coacervate polymer, in which the core is a solid, non-crystalline, core comprising a polymeric matrix containing a crystallizable water insoluble agrochemical selected from the group consisting of herbicides, semiochemicals, pesticides, plant growth regulators and nutrients and the amount of polymeric matrix is at least 20% by weight based on the weight of agrochemical and such that crystallization of the agrochemical in the core is substantially prevented.

40. A composition according to claim 39 which has been made by providing a solution in volatile organic solvent of the said active ingredient and the said polymeric matrix, forming a dispersion of particles substantially all below 10 $\mu$m in size of said solution in an aqueous solution of the said at least one coacervating polymer and thereby coating the particles by coacervation to form the said polymer coacervate shell, and distilling the dispersion to remove the said volatile organic solvent after formation of the said polymeric shell.

41. An agricultural composition that is an aqueous concentrate that is dilutable with water to form a sprayable composition that comprises a substantially stable dispersion in an aqueous medium of particles that are substantially all below 10 $\mu$m in size and that each comprise a core enclosed within a polymeric coacervate shell formed from at least one coacervate polymer, in which the core is selected from the group consisting of fluid cores and solid, non-crystalline cores comprising a polymeric matrix containing a crystallizable water insoluble agrochemical selected from the group consisting of herbicides, semiochemicals, pesticides, plant growth regulators and nutrients and in which the said polymer coacervate shell stabilizes the particles against agglomeration in the aqueous medium as a result of having a negative zeta potential that is numerically greater than $-30$ mv.

* * * * *